United States Patent [19]

Jory

[11] 4,309,775
[45] Jan. 12, 1982

[54] VISOR FOR GOGGLES AND METHOD OF ATTACHMENT

[76] Inventor: Robert L. Jory, 8525 W. 55th Dr., Arvada, Colo. 80004

[21] Appl. No.: 181,266

[22] Filed: Aug. 25, 1980

Related U.S. Application Data

[63] Continuation-in-part of Ser. No. 94,519, Nov. 15, 1979, abandoned.

[51] Int. Cl.³ ............................ A61F 9/02; A61F 9/04
[52] U.S. Cl. ............................................. 2/12; 2/432
[58] Field of Search ........................... 2/432, 12, 13

[56] References Cited

U.S. PATENT DOCUMENTS

| | | | |
|---|---|---|---|
| 757,854 | 4/1904 | Wickersham | 2/12 |
| 1,190,567 | 7/1916 | Malcom | 2/12 |
| 1,879,216 | 9/1932 | Hannan et al. | 2/12 |
| 2,286,269 | 6/1942 | Gilmartin | 2/12 |

FOREIGN PATENT DOCUMENTS

| | | | |
|---|---|---|---|
| 482554 | 7/1953 | Italy | 2/12 |
| 20678 | of 1903 | United Kingdom | 2/12 |
| 290771 | 5/1928 | United Kingdom | 2/12 |

*Primary Examiner*—Peter P. Nerbun
*Attorney, Agent, or Firm*—O'Rourke & Harris

[57] ABSTRACT

An independent readily attachable visor member for goggles having a rim portion with slots defined therein on the sides thereof to accept a strap, the visor member being formed of a pliable sheet material and formed into a relatively rigid structure by curving the visor brim portion to provide structural rigidity, positioning end mounting sections formed on the ends of the brim portion to a position substantially normal to that of the brim, such that the end sections may be inserted obliquely through the strap slots defined in the rim, and the visor member rotated to lock the brim portion against the goggle with the end sections securely engaged in the strap slots.

6 Claims, 4 Drawing Figures

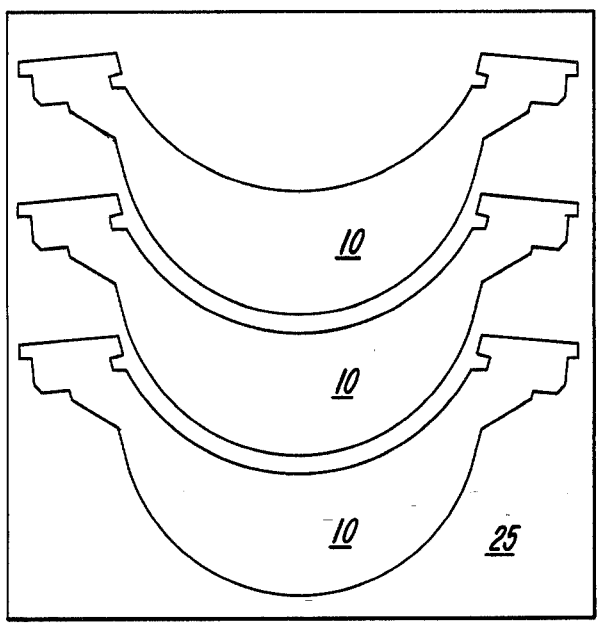
Fig_2
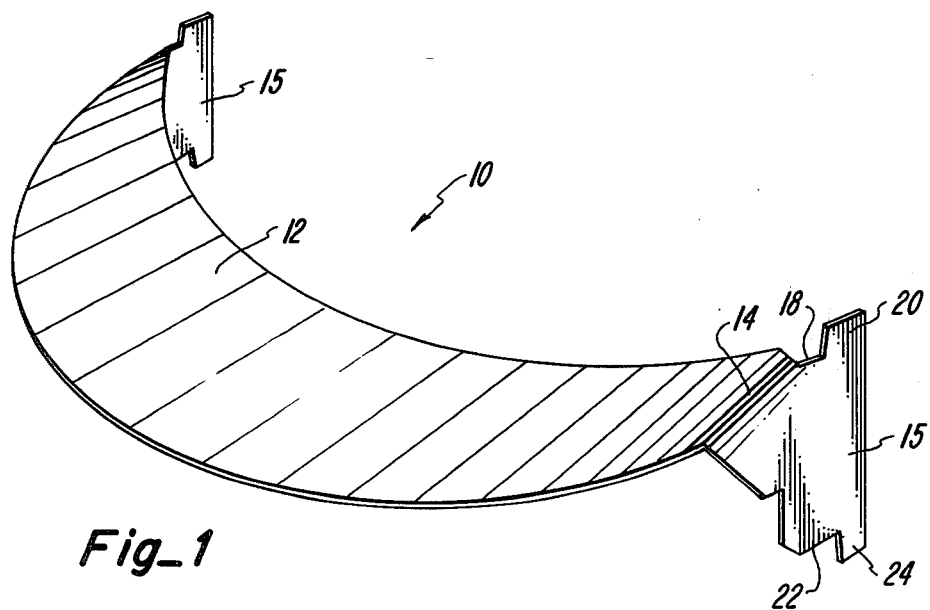
Fig_1

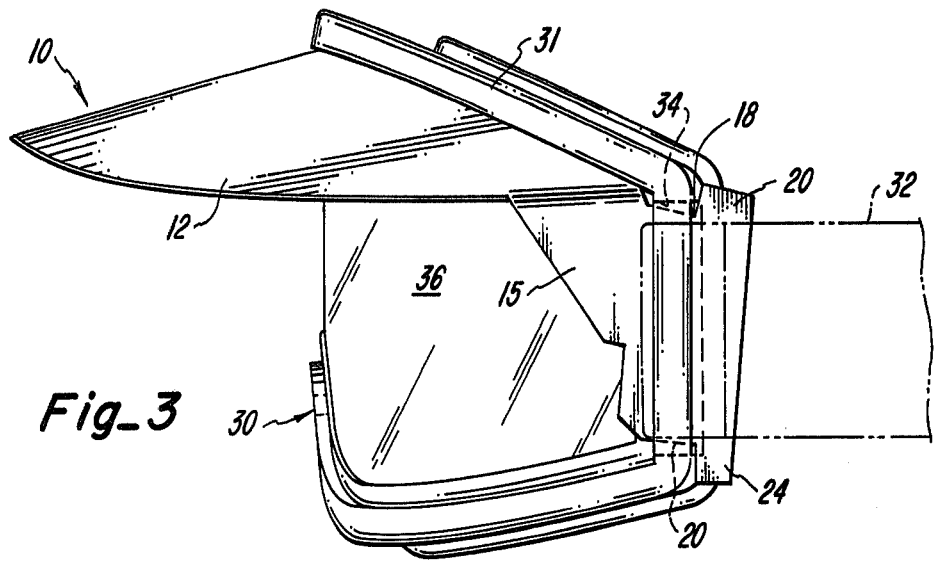
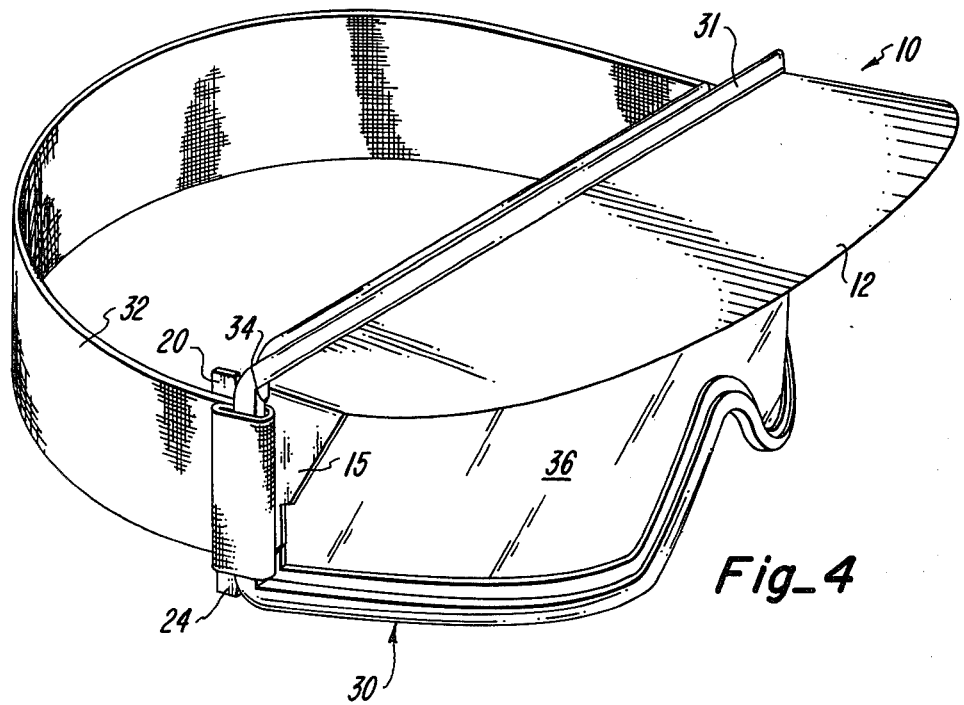

VISOR FOR GOGGLES AND METHOD OF ATTACHMENT

RELATED APPLICATION

This application is a continuation-in-part application of copending application, Ser. No. 094,519, entitled "Visor for Goggles and Method of Attachment," filed Nov. 15, 1979 now abandoned.

The present invention relates generally to visors, and more particularly to a lightweight, removable visor member adapted to be secured to a separate goggle, such as ski goggles, the visor member being formed of lightweight, pliable material, and preferably from sheet material, but being formable into a relatively rigid structure when attached to the goggle by curving the brim portion and inserting the end sections of the visor member through strap openings defined in the goggle rim, and securing the end sections in such openings.

DESCRIPTION OF THE RELATED ART

It is common for participants in vigorous activities, such as skiing, motorcycle riding, flying, or construction work to wear goggles to protect their eyes from wind, glare, or flying objects. In most instances, it is also desirable to provide a visor to shade the wearers eyes from the sun and resulting glare. However, given the weight of goggles and the at least minor discomfort of wearing a mounting strap therefore, it is generally regarded as cumbersome to wear yet another strap to secure a visor to the wearers head. Attempts to secure a visor member to the goggles has not heretofore met with universal success.

U.S. Pat. No. 3,011,170, discloses an eyeshade structure adapted to be clipped to eyeglasses by a resilient mount. However, such attachment clearly is suitable only for relatively passive activities, and would not suffice to secure the eyeshade for vigorous activities such as those mentioned above. Also, the eyeshade must be sufficiently strong to maintain it's shape and form as a free standing article. Thus, the projection of the eyeshade from the eyeglass tends to be limited by weight considerations as well as the "clip" mounting. Often a large visor is desireable, and the patented eyeshade would not serve this purpose.

Various structures and shields, such as those described in U.S. Pat. Nos. 1,701,015 and 3,274,614 are not in fact visor structures, though portions of the shield may function as visors. While such shields are structurally strong, they also involve penalties concerning weight and comfort which again the shields are not particularly suitable for robust activities. Integral shields do not have the advantage of a removable visor which may be attached or removed for varying conditions.

U.S. Pat. No. 3,931,646, discloses a goggle structure which, while not including a visor member, discloses an auxilliary lens which illustrates the skill of the art as to attachment of accessories to goggles. More specifically, the auxilliary member is attached by means of straps and snaps, and must be of adequate strength, with accompanying weight, to maintain the desired form. Again, a contilevered visor member would not be suitably supported by the patented means.

In summary, the related art recognizes the need to attach auxilliary members, such as visors, to a primary support worn adjacent the wearers eyes, but, on the basis of the related art noted, makes no teaching of a means for securely attaching lightweight members such as visors.

SUMMARY OF THE INVENTION

The present invention, which provides a heretofore unavailable structure and method for attaching a visor member to conventional goggles, comprises a relatively lightweight, pliable visor member, preferably formed from planar sheet material, which is curved and/or bent to form a relatively rigid structure, and may be securely attached to conventional goggle rims at slots defined therein to accept an elastic head strap by inserting mounting portions of the visor having notches defined therein through the slots at an angle, and then rotating the member to engage the end portion securely in the rim slot. As a result of the curvature imparted to the brim portion of the visor, and the appropriate fitting of the rear portion of the brim against the adjacent goggle rim and/or lens, a lightweight, securely attached and functionally rigid visor is provided.

Accordingly, it is an object of the present invention to provide a lightweight, securely attachable visor member for use with conventional goggles, such as ski goggles.

Another object of the present invention is to provide a method for conveniently and effectively mounting a visor member of pliable material to conventional goggles in such a manner as to securely attach the visor member while concurrently lending structural rigidity to the visor.

Yet another object of the present invention is to provide removable visor member configured in such a manner as to be formed of flat, sheet material, and thereafter formed into a three dimensional structurally rigid visor member suitable for withstanding substantial deforming forces, such as from wind.

These and other objects and features of the present invention will become apparent from the following description.

BRIEF DESCRIPTION OF THE DRAWINGS

In the drawings:

FIG. 1 is a perspective view of a visor member in accordance with the instant invention in which the visor member is configured in a rigid arrangement such as when mounted to goggles;

FIG. 2 is a view of a plurality of visor members such as shown in FIG. 1 as initially formed from planar sheet material;

FIG. 3 is a side view of the visor member of FIG. 1 mounted on goggles; and

FIG. 4 is a perspective view of a visor member and goggle arrangement as set forth in FIG. 3.

DETAILED DESCRIPTION OF THE DRAWINGS

Turning now to the drawings, wherein like components are designated by like numerals throughout the various figures, a visor member appropriate for mounting to conventional goggles is illustrated in FIG. 1 and generally designated by the reference numeral 10. Visor member 10 includes curved brim portion 12, which of course functions as the shading portion of the visor, and, with regard to one end section with the understanding the other end section is substantially identical, crease 14 defined at the end of brim portion 12 such that mounting section 15 extends substantially perpendicular to the primary direction in which brim portion 12 extends. Mounting section 15 has defined therein upper notch 18, which serves to define upper mounting tab 20 and lower notch 22 which serves to define lower mounting tab 24. Mounting section 15 may be positioned as described with a smooth curve as well as with a defined crease 14.

As shown in FIG. 2, visor member 10 may be readily formed from pliable sheet material 25, as by die stamping. While sheet material 25 is pliable, a certain amount of stiffness such as from polymeric sheet material, or heavy paperboard, such as bristol board, is preferred. Though, when in the flat configuration, visor member 10 is readily distendable to various shapes, when, with reference to FIG. 1, visor member 10 is curved along brim portion 12 and supported at the rear edge between end sections 15, the normally pliable sheet material becomes functionally rigid as a result of such curvature and tensioning, and thus is able to withstand wind and other such forces when in place. This will be more readily understood with reference to FIGS. 3 and 4.

As shown in FIG. 3, goggle 30, which is of conventional and known construction, includes a rim portion 31, a resilient head band 32 attached to rim 31 at slots 34 defined through rim 31, and lens portion 36. Visor member 10 mounts with end sections 15 extending through slots 34 such that notches 18 and 22 engage the upper and lower portions of the slot respectively, and upper and lower mounting tabs 20 and 24 bear against rim 31 at slots 34. In this manner, brim 12 is urged against the interface of rim 31 and lens 36 with the curvature of lens 36 complementary to the adjacent curvature of brim portion 12. Visor member 10 may also bear against rim 31 above lens 36. Thus visor member 10 is attached to goggle 30 in such a manner that, as a combined result of the prestressing of visor member 10 by the locking action of notches 18 and 22 in slots 34, the support afforded by lens 36 and rim 31 at the rear edge of brim portion 12, and the curvature of brim portion 12, visor member 10 becomes functionally rigid well beyond the rigidity of visor member 10 alone, and is securely attached to goggles 30.

It will be noted that the mounting sections 15 of visor member 10 are of a greater vertical dimension, as shown in FIG. 3, than horizontal dimension, with reference to the lower portions thereof. Accordingly, attachment and detachment of visor member 10 is readily facilitated, by, again with reference to FIG. 3, rotating visor member 10 of pliable material downward away from rim 31 thereby bringing the smaller dimension of mounting sections 15 into position for movement out of or into slots 34. For mounting, the smaller dimension of mounting sections 15 are first inserted through slots 34 of goggle 30, and then the entire visor member 10 is rotated, with reference to FIG. 3, in a clockwise direction such that the greater, elongated dimension of mounting sections 15 is brought to bear against slots 34 with notches 18 and 22 engaging the rear portion thereof to secure visor member 10 to goggle 30.

Alternatively, mounting tabs 20 and 24 may be resiliently bent while inserting mounting sections 15 through slots 34, and then allowed to again extend as shown in FIG. 3. This method is less desirable in that tabs 20 and 21 may fatigue and break if bent excessively.

It is anticipated that the visor member in accord with the instant invention may be made of various materials, either colored or clear, transparent or opaque, or may bear, for instance, logos or other decorative matter thereon. While minor variations in specific configuration may be required to adapt visor member of the instant invention to fit goggles of different manufacture, in view of the fact that slots or similar openings, and headbands are essentially universally employed to hold goggles to a wearers head, it is clear that the visor member may be adapted to fit goggles of almost any manufacture or purpose including skiing, motorcycle riding, aviation, etc.

Although but one embodiment of the present invention has been illustrated and described, it is apparent that various changes and modifications will be readily accomplished by those skilled in the art and such changes may be made without departing from the scope of the invention as defined by the following claims.

What is claimed is:

1. A visor member adapted to be secured to goggles including a lens, a rim supporting the lens and having elongated openings defined therethrough on opposite sides thereof and extending through the rim in a direction substantially transverse to the lens, and an elastic headband attached to the rim at the ends of the headband at the openings in the rim, the visor member comprising:

a brim portion having a front edge and a rear edge, the rear edge being configured to complementarily engage the upper portion of the goggles; and opposed visor member end mounting sections extending from the sides of the brim portion in a direction substantially perpendicular thereto, the end sections including upper and lower notches defined therein and delineating upper and lower mounting tabs, the dimension of the mounting tabs being greater than the largest dimension of the goggle rim elongated openings whereby the mounting tab may bear upon the rear upper and lower edges of the openings to securely mount the visor member to the goggles;

whereby the visor member may be secured to the goggles by engaging the rear edge of the brim portion at the upper portion of the goggles, and tensioning the brim portion thereagainst by means of the end mounting sections engaged in the openings of the goggle.

2. A visor member as set forth in claim 1 in which the visor member is a unitary member formed of pliable sheet material and adapted to form a substantially rigid structure by inducing a curvature in the brim portion when mounting the visor member to goggles.

3. A visor member as set forth in claim 2 in which the end mounting sections are by a crease and extend substantially perpendicular to the brim portion to further provide rigidity to the visor member.

4. A visor member adapted to be mounted upon goggles including a lens, a rim at least partially surrounding the lens and having elongated openings extending therethrough in a direction substantially perpendicular to the lens portion defined in opposite sides thereof, and an elastic headband engaged in the openings, the visor member comprising:

a pliable planar sheet including a central brim portion and opposed end mounting sections, the brim portion having a front edge and a rear edge with the rear edge being adapted to engage the goggles at the upper portion thereof; and opposed end mounting sections defined of the sheet material and extending substantially perpendicular to and rearward of the brim portion, the end mounting sections including a pair of mounting tabs defined one each on the upper and lower portions of each end mounting section with the dimension between the mounting tabs being greater than the complementary dimension of the rim openings;

whereby the pliable sheet material defining the visor member may be formed into a rigid structure by curving the brim portion, engaging the rear edge of the brim portion against the upper portion of the goggles, and tensioning the brim portion against the goggle by inserting the pliable end mounting sections through the rim openings with the tabs bearing against the upper and lower edges of the rim openings.

5. A method of mounting a pliable visor member to goggles having a lens, a rim at least partially surrounding the lens and including elongated openings defined through the rim on opposite sides thereof in a direction substantially normal to the lens surface, and an elastic headband engaged in the openings, the method comprising:

bending each end portion of a pliable, planar sheet material forming the visor member to define opposed end mounting portions extending substantially perpendicular to and rearward of the brim portion of the visor member defined therebetween, the end mounting sections each including a pair of upper and lower deformable mounting tabs;

inserting the thus defined end sections one each through each of the elongated openings defined at the side portions of the rim by deforming the tabs to position the end section with the tabs bearing against the rear surface defined in the elongated openings; and defining a curve in the brim portion of the visor member and engaging the rear edge of the brim portion adjacent the upper portion of the goggle;

whereby, the pliable, planar material forming the visor member is configured to a functionally rigid member attached to the goggle.

6. A method of mounting a pliable visor member as set forth in claim 5 in which the opposed end mounting sections are of a greater dimension in the direction perpendicular to the brim portion than in the direction substantially parallel to the brim portion and the visor member is mounted by inserting the end mounting sections through the elongated opening with the lesser dimension of the end mounting sections being presented at the opening, and thereafter rotating the visor member to bring the greater dimension of the end mounting section in contact with the elongated openings with the rear edge of the brim portion bearing adjacent the upper portion of the goggles.

* * * * *